(12) United States Patent
Guo et al.

(10) Patent No.: US 12,380,386 B2
(45) Date of Patent: Aug. 5, 2025

(54) SYSTEM FOR BUILDING-SPECIFIC MULTI-PERIL RISK ASSESSMENT AND MITIGATION

(71) Applicant: Kinetica Dynamics Inc., Toronto (CA)

(72) Inventors: Wen Wei Jack Guo, Toronto (CA); Constantin Christopoulos, Toronto (CA); Michael Montgomery, Toronto (CA)

(73) Assignee: Kinetica Dynamics Inc., Toronto (CA)

( * ) Notice: Subject to any disclaimer, the term of this patent is extended or adjusted under 35 U.S.C. 154(b) by 979 days.

(21) Appl. No.: 17/492,455

(22) Filed: Oct. 1, 2021

(65) Prior Publication Data

US 2023/0106956 A1 Apr. 6, 2023

(51) Int. Cl.
*G06Q 10/0635* (2023.01)
*B01J 23/42* (2006.01)
(Continued)

(52) U.S. Cl.
CPC ......... *G06Q 10/0635* (2013.01); *E04H 9/027* (2013.01); *G06N 7/01* (2023.01); *B01J 23/42* (2013.01); *B01J 23/44* (2013.01); *B01J 31/06* (2013.01); *B01J 31/165* (2013.01); *B01J 31/226* (2013.01); *B01J 35/393* (2024.01); *B01J 35/45* (2024.01); *B01J 37/0201* (2013.01); *B01J 37/0211* (2013.01); *B01J 37/16* (2013.01); *B01J 37/343* (2013.01); *B01J 2231/645* (2013.01);
(Continued)

(58) Field of Classification Search
CPC ... B01J 31/06; B01J 23/44; B01J 23/42; B01J 2235/00; B01J 2235/30; B01J 37/0211; B01J 37/16; B01J 2231/645; B01J 2531/0211; B01J 2531/824; B01J 31/226; B01J 31/165; B01J 35/393; B01J 35/45; B01J 37/343; B01J 37/0201; C07C 5/09; C07C 2523/44; C07C 2531/06; C07C 7/167; C08F 26/06; Y02P 20/52; G06Q 10/0635; E04H 9/027; G06N 7/01
See application file for complete search history.

(56) References Cited

U.S. PATENT DOCUMENTS

| | | | |
|---|---|---|---|
| 7,769,608 B1 * | 8/2010 | Woll | G06Q 40/08 705/4 |
| 2013/0226624 A1 * | 8/2013 | Blessman | H04N 7/181 705/4 |
| 2017/0161859 A1 | 6/2017 | Baumgartner | |

* cited by examiner

*Primary Examiner* — Quoc A Tran
(74) *Attorney, Agent, or Firm* — Wilson Lue LLP; Jenna L. Wilson

(57) ABSTRACT

A system for building-specific multi-peril risk assessment and mitigation is disclosed. The system comprises a multi-peril hazard module, a processor, a database and a graphical network module. The multi-peril hazard module is configured to obtain hazard information and create a multi-peril event catalogue configured to generate intensity measures for multiple perils. The processor is configured to derive a peril vulnerability function and determine building-specific risk assessment results based on the hazard information and the peril vulnerability function. The database is configured to store the derived plurality of peril vulnerability functions. The graphical network module is configured to create probabilistic networks, wherein the probabilistic networks are connected to the determined building-specific risk assessment results of the peril vulnerability functions that have strong interdependencies and determine a multi-peril risk associated with the building.

21 Claims, 7 Drawing Sheets

(51) Int. Cl.
*B01J 23/44* (2006.01)
*B01J 31/06* (2006.01)
*B01J 31/16* (2006.01)
*B01J 31/22* (2006.01)
*B01J 35/30* (2024.01)
*B01J 35/45* (2024.01)
*B01J 37/02* (2006.01)
*B01J 37/16* (2006.01)
*B01J 37/34* (2006.01)
*C07C 5/09* (2006.01)
*C07C 7/167* (2006.01)
*C08F 26/06* (2006.01)
*E04H 9/02* (2006.01)
*G06N 7/01* (2023.01)

(52) U.S. Cl.
CPC ........ *B01J 2235/00* (2024.01); *B01J 2235/30* (2024.01); *B01J 2531/0211* (2013.01); *B01J 2531/824* (2013.01); *C07C 5/09* (2013.01); *C07C 7/167* (2013.01); *C07C 2523/44* (2013.01); *C07C 2531/06* (2013.01); *C08F 26/06* (2013.01); *Y02P 20/52* (2015.11)

SYSTEM FOR BUILDING-SPECIFIC MULTI-PERIL RISK ASSESSMENT AND MITIGATION

BACKGROUND

Field

The disclosed subject matter relates to the field of risk assessment. More particularly, but not exclusively, the subject matter relates to asset-specific multi-peril risk assessment and mitigation.

Discussion of Related Field

Natural hazard risk analysis in real asset portfolios is a field that is currently dominated by the insurance industry who utilizes a class of analytical models called "catastrophe models" or CAT models for the determination of portfolio losses and associated costs for offering coverage against natural perils. In general, all CAT models comprise of four different modules: hazard, exposure, risk and financial. The hazard module makes scientific predictions of intensity measures associated with the peril of interest given relevant geological and meteorological inputs; the exposure module contains the value and spatial distribution of assets in the region of interest; the risk module performs the calculation of loss given hazard and exposure using vulnerability functions; the financial module computes the financial impact of the risk given insurance policy and coverage details. CAT models are primarily oriented towards insurance and reinsurance users and the methodology for evaluating natural hazard risk is suitable for insurance portfolios typically containing thousands to hundreds of thousands of spatially distributed assets. While the combination of hazard, exposure and risk modules can be adopted to perform loss analysis on an asset portfolio of arbitrary size, due to the requirement for CAT models to handle large portfolios efficiently, the evaluation of loss at the individual asset level is extremely crude and has low accuracy and reliability when extrapolated to the individual asset level. This is not an issue for most insurers as high-resolution risk output at the asset level is not very meaningful compared to the aggregated risk metrics derived from the entire exposed portfolio. However, the same cannot be said for owners of individual assets or portfolios, who may require high-resolution and reliable data to inform them on means of risk management that go beyond property and casualty insurance.

High resolution risk analysis stems from the advancement in performance-based engineering concepts first developed by earthquake engineers in the early 2000's. The basic idea of performance-based earthquake engineering (PBEE) is to develop a set of theoretical tools that enables engineers to derive results that are directly relevant to the decision-making of owners of the assets exposed to seismic hazard. A direct consequence of this is that deliverables of performance-based engineering analysis can provide quantitative decision-metrics such as financial impacts, downtime and casualty, rather than technical results that address code adequacy, which has been the primary objective for engineers prior to PBEE. To do this, a probabilistic framework that integrates hazard and physics-based damage and loss assessment of structures to such hazards has been developed and codified through various design standards.

By integrating methodologies employed in PBEE and in CAT models, such concepts can be expanded to cover portfolio level analysis involving multiple spatially distributed assets for detailed risk, and mitigation analysis that provides accurate quantitative performance and cost-benefit metrics that are directly relevant for the management of risk in an asset-specific context. This has been formulated and implemented by Kinetica Risk in the past for earthquake risk.

However, there is presently no platform for accounting for multiple perils that can impact building portfolios, in a statistically consistent meaningful manner. In other words, owners of both public and private real asset portfolios lack a unified tool that enables them to examine multiple natural hazard risk through their own business lens, and make informed financial, operational and risk management decisions for their assets, which is crucial for navigating the physical challenges that a changing climate, and increasingly urbanizing environment poses.

In light of the above, it is apparent that there is a need for a methodology and implementation of a multi-hazard platform for evaluating risk and resilience of real asset portfolios in a time and cost-efficient manner.

SUMMARY

In one embodiment a system for building-specific multi-peril risk assessment and mitigation is disclosed. The system comprises a multi-peril hazard module, a processor, a database and a probabilistic graphical network module. The multi-peril hazard module is configured to obtain hazard information related to one or more buildings (a portfolio of buildings) for multiple perils, and create a multi-peril event catalogue for the multiple perils, wherein the multi-peril event catalogue is configured to generate intensity measures for each of the multiple perils on a event-by-event basis. The processor is configured to select a set of peril vulnerability functions from a pre-generated database of vulnerability functions for each of the multiple perils based on representative archetypes of the buildings in the portfolio, wherein each peril vulnerability function relates to a consequence of interest corresponding to a building archetype. Further, the processor is configured to determine building-specific risk assessment results for each building based on the hazard information and the peril vulnerability functions by simulating events in the catalogue. The pre-generated vulnerability database stores the derived plurality of peril vulnerability functions for the multiple perils corresponding to each of the archetypes of buildings, which can be generated using performance-based engineering analysis. The probabilistic graphical network module is configured to create probabilistic networks, wherein the probabilistic networks are connected to the determined multi-peril building-specific risk assessment results to model impacts to processes that have strong interdependencies on different consequences in a single building, or between different consequences across multiple buildings in the portfolio, on an event-by-event basis.

BRIEF DESCRIPTION OF DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form a part of the detailed description. The drawings show illustrations in accordance with example embodiments. These example embodiments, which may be herein also referred to as "examples" are described in enough detail to enable those skilled in the art to practice the present subject matter. However, it may be apparent to one with ordinary skill in the art, that the present invention may be practised without these specific details. In other instances, well-known methods, procedures and components have not been described in detail so as not to unnecessarily obscure aspects of the embodiments. The embodiments can be combined, other embodiments can be utilized, or structural, logical, and design changes can be made without departing from the scope of the claims. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated.

Figure 1:
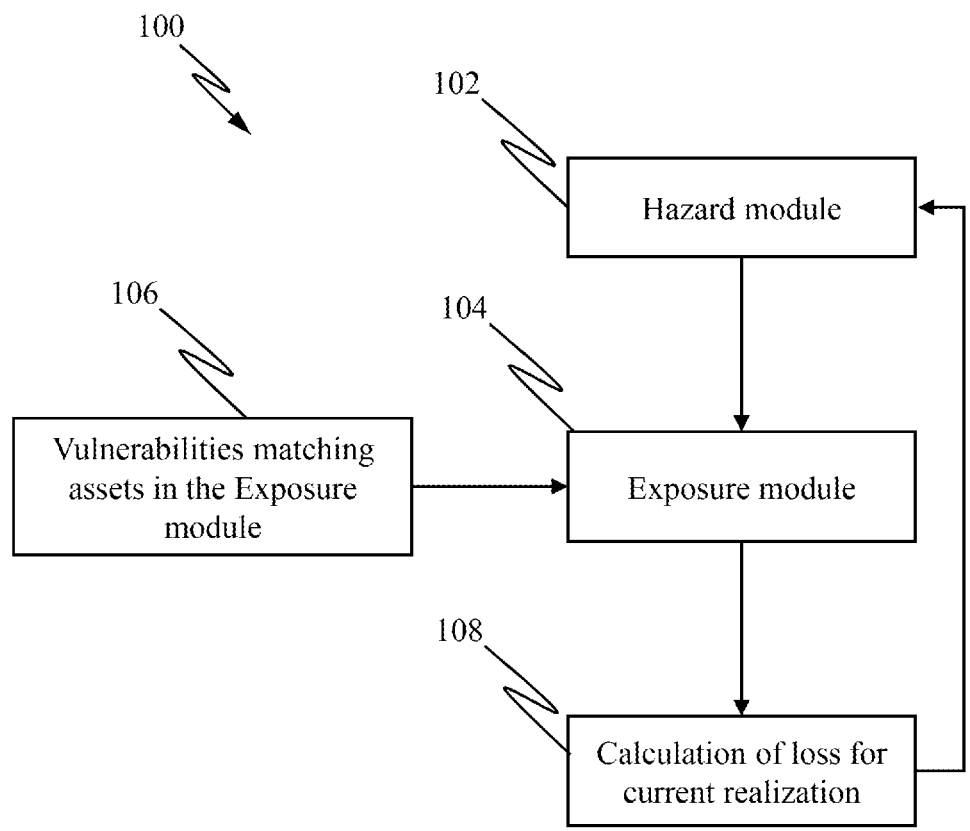
FIG. 1 illustrates a conventional catastrophe (CAT) model 100, in accordance with an embodiment.

FIG. 1 illustrates a conventional catastrophe (CAT) model process, in accordance with an embodiment. Most CAT models have three modules that supports the calculation of ground up losses: namely, a hazard module 102, an exposure module 104 and a vulnerability module 106. Typically, the exposure module 104 describes the portfolio of structures by their specific location, building attributes such as year built, type of construction, number of storeys, other optional modifiers such as whether the building meets code requirements associated with the peril of interest. In an assessment, a hazard intensity measure (IM) is generated either by a numerical model of the physical process giving rise to the peril of interest or based on historical data (hazard module 102), and the IM is used to calculate the likelihood of each building experiencing a certain level of loss (vulnerability module 106). This process is repeatedly performed, over many realizations and many number of years until the desirable return period is achieved. For instance, a model may generate 10,000 one-year simulations of a hazard. For each one-year simulation, there could be no events, a single event or multiple events with different losses. After 10,000 of such one-year simulations, the largest loss realized would correspond to a 1 in 10,000 year loss. Other types of risk metrics such as the average annualized loss and the tail value at risk can also be computed from the event results.

A major shortcoming of CAT models is that the individual asset vulnerabilities are inherently simple in order to facilitate large portfolio sizes. These vulnerabilities are typically described by a single loss metric (usually the loss ratio corresponding to the ratio of replacement value) which are functions of a set of general attributes, such as building type and year of construction. Hence, CAT models are usually unable to identify loss drivers, or resolve any details of the loss at the asset specific level to support risk mitigation and financial decisions relating to maintenance and capital investment. Furthermore, the asset-specific results from CAT models are also highly uncertain as they are intended to describe a much larger categories of assets corresponding to the general attributes associated with them.

More detailed loss assessments for earthquake risk is well documented through the PBEE standards such as FEMA P-58. This framework has also been extended to cover cost-benefit assessments and portfolio level analysis through an existing patent application. Recently, analogous procedures are developed sporadically in the literature for other type natural hazards, utilizing engineering methods suitable for capturing damage and losses from these hazards [flood, ARA wind]. However, a unified methodological framework is not formed that allows the integration of multiple natural hazards in risk assessment.

Figure 2:
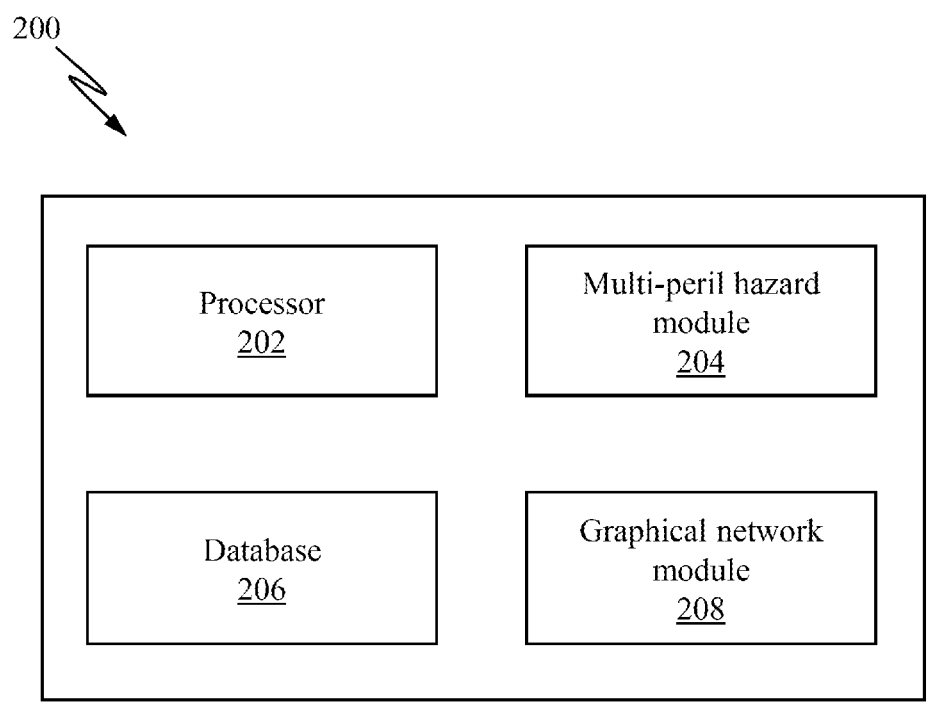
FIG. 2 illustrates a system 200 for building-specific multi-peril risk assessment and mitigation, in accordance with an embodiment.

FIG. 2 illustrates a system 200 for building-specific multi-peril risk assessment and mitigation, in accordance with an embodiment. The system may comprise a processor 202, a multi-peril hazard module 204, a database 206 and a probabilistic graphical network module 208. The system 200 may facilitate high-resolution risk analysis that provides portfolio-specific performance metrics for most portfolios without the need for detailed engineering analysis, which will be reserved for highly unique building portfolios.

The processor 202 may be implemented in the form of one or more processors 202 and may be implemented as appropriate in hardware, computer-executable instructions, firmware, or combinations thereof. Computer-executable instruction or firmware implementations of the processor 202 may include computer-executable or machine-executable instructions written in any suitable programming language to perform the various functions described.

The database 206 may include a permanent memory such as hard disk drive, may be configured to store data, and executable program instructions that are implemented by the processor 202. The database 206 may be implemented in the form of a primary and a secondary memory. The database 206 may store additional data and program instructions that are loadable and executable on the processor 202 module 204, as well as data generated during the execution of these programs. Further, the database 206 may be volatile memory, such as random-access memory and/or a disk drive, or non-volatile memory. The database 206 may comprise of removable memory such as a Compact Flash card, Memory Stick, Smart Media, Multimedia Card, Secure Digital memory, or any other memory storage that exists currently or may exist in the future.

Figure 3:
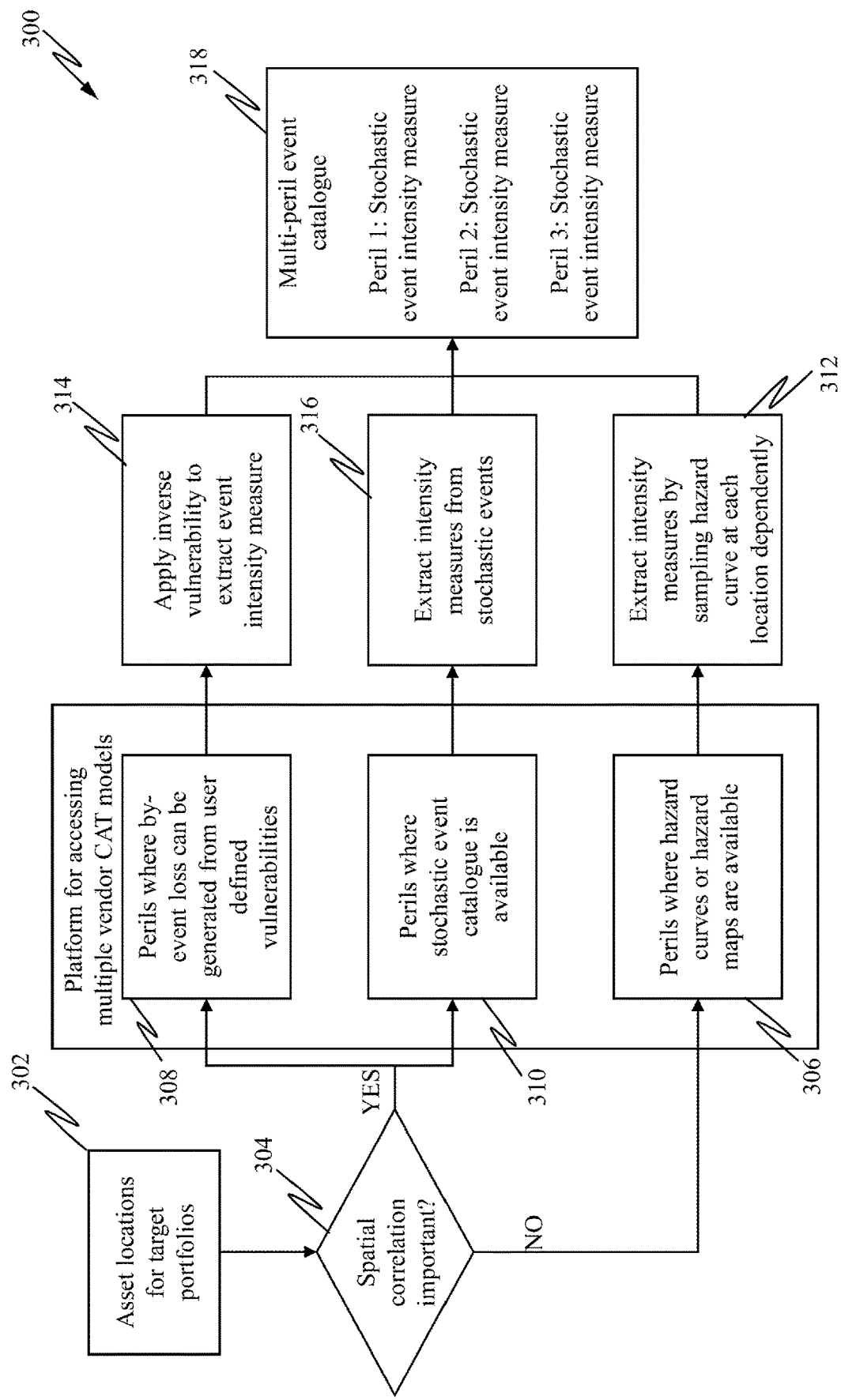
FIG. 3 illustrates compilation of multi-peril hazard data using the multi-peril hazard module 204, in accordance with an embodiment.

FIG. 3 illustrates compilation of multi-peril hazard data using the multi-peril hazard module 204, in accordance with an embodiment. The multi-peril hazard module 204 may be configured to obtain hazard information related to at least a building for multiple perils and create a multi-peril event catalogue for the multiple perils, wherein the events catalogue is configured to generate intensity measures for each of the multiple perils.

In one embodiment, the multi-peril hazard module 204 may obtain probabilistic hazard data across multiple natural perils. At step 302, the asset/building location information of the target portfolio is provided to the multi-peril hazard module 204.

In one embodiment, the multi-peril hazard module 204 may obtain the hazard information based on the received location information.

In one embodiment, the multi-peril hazard module 204 may be configured to obtain hazard information using one of the many commercial hosting platforms (e.g., NASDAQ risk modelling, QOMPLEX, EMEA). These platforms offer a unifying interface to access both hazard and risk models developed by traditional catastrophe model vendors. While the form of information may differ from one peril to another, and from one CAT model vendor to another, the hazard information can typically be extracted either through subscription to hazard maps, stochastic event catalogues, or to event-based risk models which can be converted to hazard information.

At step 304, the multi-peril hazard module 204 determines whether spatial correlation between assets/buildings is important for a gives hazard. If the spatial correlation between assets is not important, then at step 306, hazard maps at different intensities (specified by its return period) may be used to extract the required intensity measures by sampling hazard curve at each location independently at step 312.

If the spatial correlation between assets is important, then at step 308 the information pertaining to perils where by-event loss can be generated from user-defined invertible vulnerabilities or at step 310 the information pertaining to perils where stochastic event catalogue is available is used.

At step 314, the intensity measures may be extracted by applying inverse vulnerability function to the by-event risk information obtained from the platform.

At step 316, the intensity measures may be extracted from the stochastic events catalogue.

At step 318, the multi-peril hazard module 204 may be configured to create a multi-peril event catalogue configured to generate intensity measures for multiple perils.

In one embodiment, the multi-peril hazard module 204 may generate the intensity measures for different perils on a by-event basis.

In one embodiment, the multi-peril hazard module 204 may generate the intensity measures for different perils on a by-peril basis.

Thus, the multi-peril hazard module 204 may create the multi-peril event catalogue that describes the relevant intensity measures for each event, for each type of peril considered at each location of interest for multi-peril risk assessment.

Figure 4:
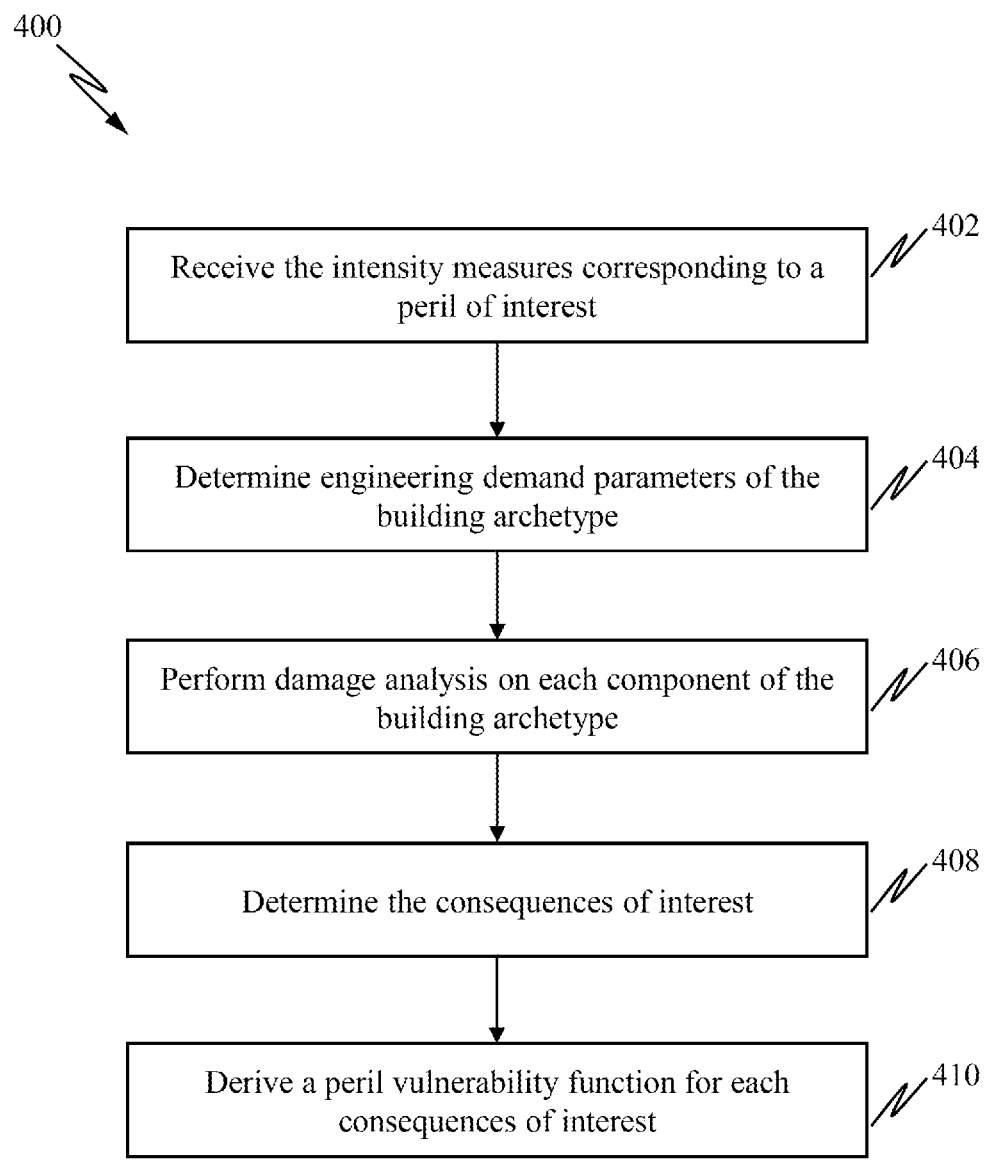
FIG. 4 is a flowchart 400 of the process of derivation of a peril vulnerability function for a building archetype, in accordance with an embodiment.

FIG. 4 is a flowchart 400 of the process of derivation of a peril vulnerability function for a building archetype, in accordance with an embodiment. This process is peril-dependent and is based on engineering analysis of individual building archetypes.

At step 402, a full range of intensity measures corresponding to a peril of interest are defined for an archetype. The peril of interest may be wind, flood, earth quake so on and so forth. As an example, the intensity measure for flood may be water depth and intensity measure for wind may be wind speed.

At step 404, engineering demand parameters of the building archetype based on the defined range of intensity measures are generated. This may be done by performing engineering analysis to quantify the engineering demand parameters which are the building response quantities that lead to component damage.

Based on this, load cases which represent physical manifestation of the hazard for each of the respective peril can be defined using engineering standards relating to the hazards of interest. Some hazards, such as fluvial flood, may not require detailed structural analysis as the building component damage is directly correlated to the water depth and content elevation. Other hazards, such as tornado, hurricanes and tsunami, may involve dynamic analysis of the building using finite element models and computational fluid dynamic models to determine the engineering demand parameters, which are response quantities that are related to the damage of different building components. This process will result in a probabilistic distribution of engineering demand parameters due to inherent uncertainties in the hazard input for a given intensity.

At step 406, damage analysis on each component of the building archetype based on the determined engineering demand parameters can be performed.

In one embodiment, the processor 202 may process the engineering demand parameters data to derive smooth joint engineering demand parameters distributions using principal component analysis. The smooth joint distributions may then be used by the processor 202 to generate individual realizations of engineering demand parameters directly correlated to the component damage in the building using peril-specific fragility and consequence functions. This process results in a high-resolution building-specific loss evaluation applicable to multiple different natural perils.

In one embodiment, the processor 202 may perform damage analysis through Monte Carlo sampling using engineering demand parameters on each individual component in the building of interest using the component-specific fragility.

At step 408, the processor 202 may determine the consequences of interest and aggregate all the loss across all the components to arrive at a final loss distribution for a given peril and a given hazard intensity.

The consequences of interest may be downtime, casualty and other functional processes that may be impacted by component damage.

At step 410, the processor 202 may derive a peril vulnerability function of each of the consequences of interest corresponding to the peril of interest.

In one embodiment, the processor 202 may repeat steps 406 to 410 for multiple hazard intensities to derive the peril-specific vulnerability functions (loss versus intensity input) for a single building archetype.

Figure 5:
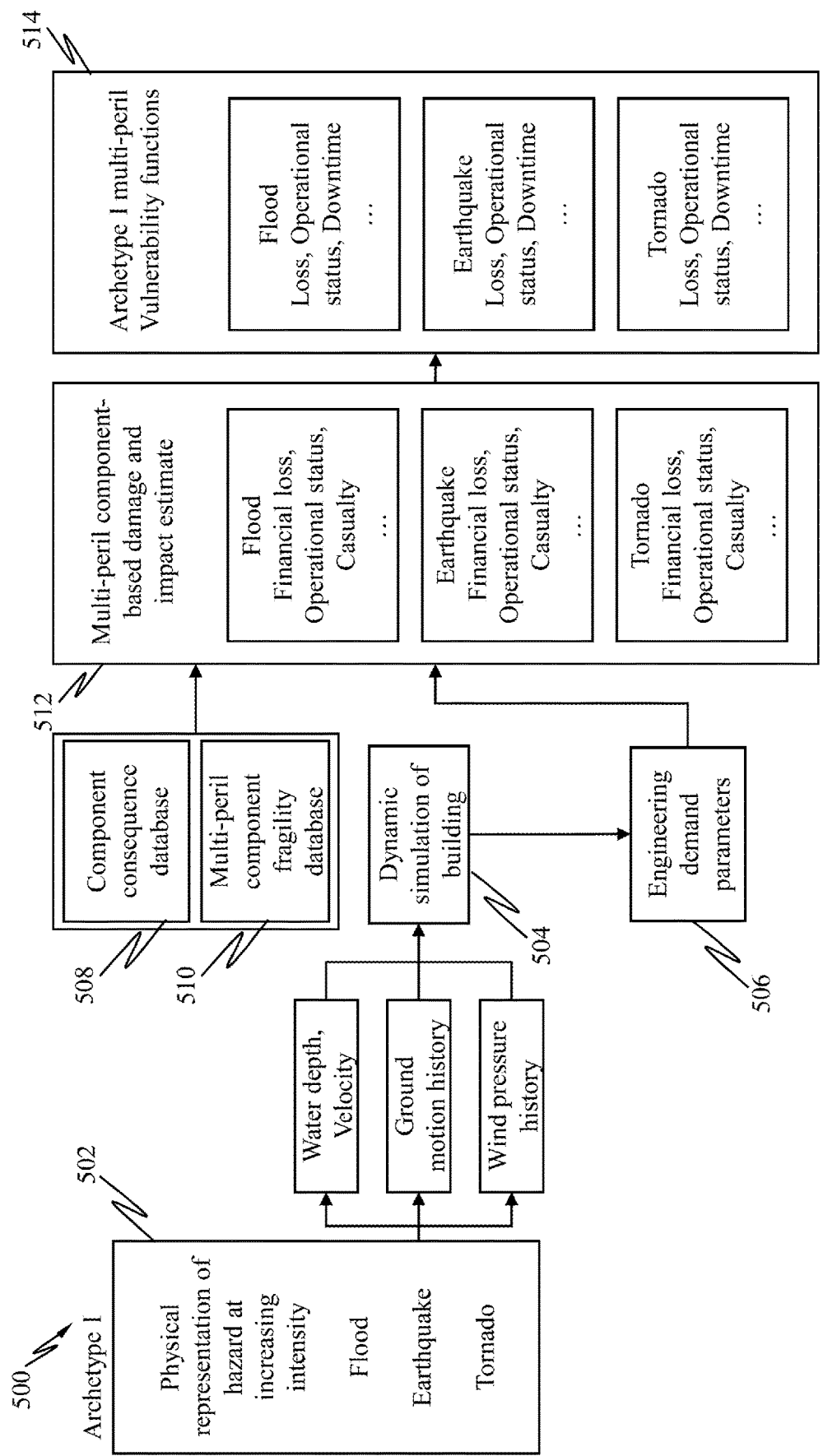
FIG. 5 illustrates the database 206 comprising multi-peril vulnerability functions for each archetype of the building, in accordance with an embodiment.

FIG. 5 is an elaborated process for generating peril-specific vulnerability functions for each building archetype that are stored in database 206, in accordance with an embodiment. Engineering demand parameters generated from dynamic simulations and peril-specific component fragility and consequence databases may be used by processor 202 to perform damage and risk simulations of to the building structure, building roof and exterior closure, in order to define the peril-specific vulnerabilities for each building archetype.

In one embodiment, the dynamic analysis 504 may be performed using finite element analysis, computational fluid dynamic simulation or the like. The processor 202 may use the engineering demand parameters 506 based on the dynamic analysis in conjunction with component fragility and consequences to derive peril-specific vulnerabilities.

In one embodiment, the peril-specific vulnerabilities in database 206 may be generated by processor 202 using a component fragility database 510 comprising fragility functions and a consequence database 508 comprising consequence functions.

The processor 202 may determine multi-peril component based damage and impact 512 based on the engineering demand parameters, consequence functions and peril-specific fragility information. The processor 202 may determine the consequences of interest for the peril of interest and may derive a peril vulnerability functions 514 for each of the consequences of interest for the peril of interest.

The database 206 may store the multi-peril vulnerability functions for multiple perils corresponding to a building archetype. Similarly, the database 206 may store the multi-peril vulnerability functions 516 for multiple building archetypes.

The processor 202 may be configured to determine building-specific risk assessment results based on the hazard information and the peril vulnerability function obtained from database 206.

Figure 6:
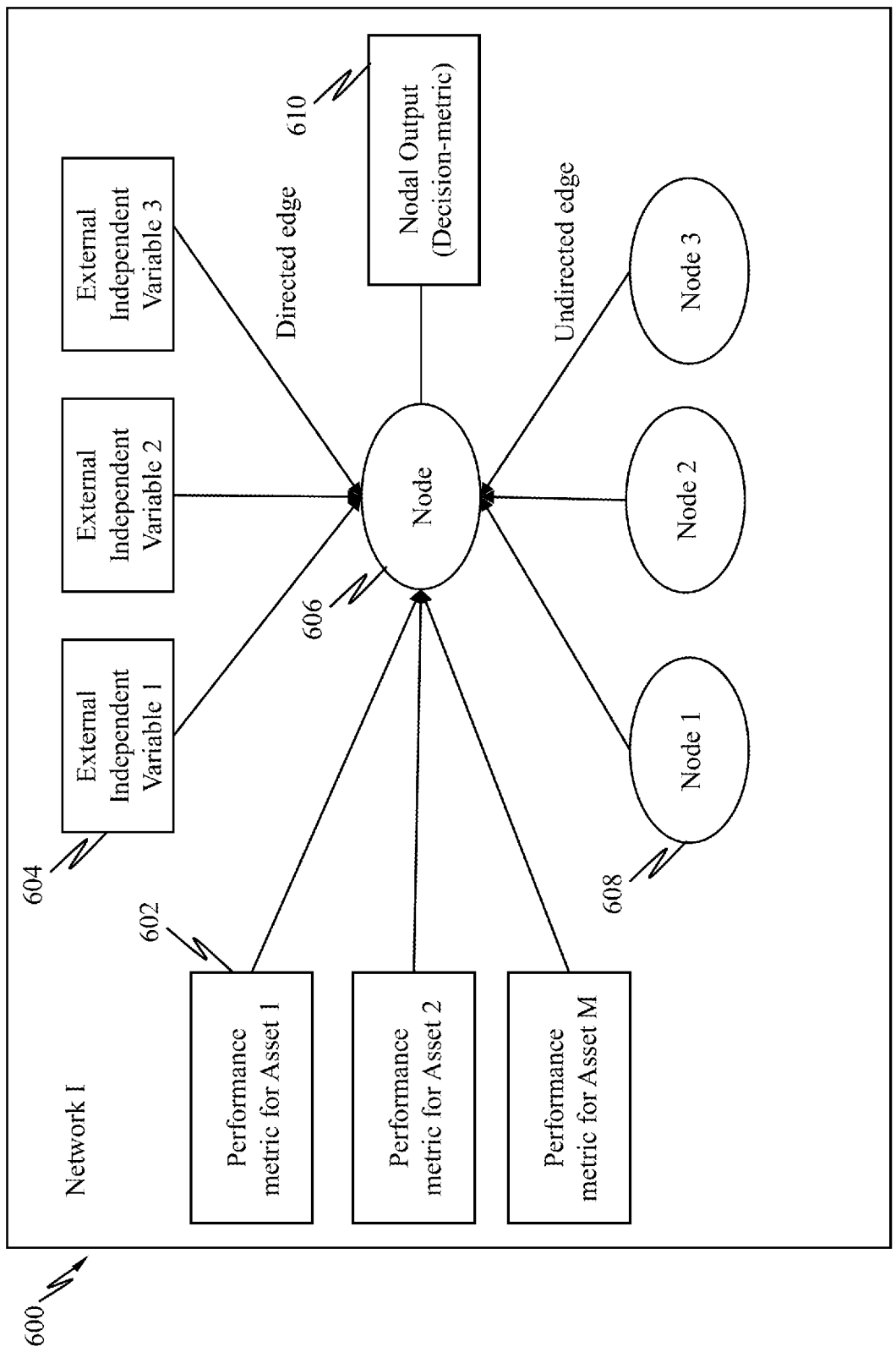
FIG. 6 illustrates a probabilistic network 600 created by the graphical network module 208, in accordance with an embodiment.

FIG. 6 illustrates a probabilistic network 600 created by the probabilistic graphical network module 208, in accordance with an embodiment. The probabilistic graphical network may be integrated with the building loss metrics to predict the impact to interdependent processes. The probabilistic networks are directly connected to the building-specific risk assessment results (asset performance metrics) generated from the high-resolution peril vulnerability functions of each asset to model processes that have strong interdependencies.

In one embodiment, multiple networks may be defined to capture different decision-metrics of interest 610 represented by an output node 606. This node may be connected via a directed edge to a number of independent variables 604. Independent variables 604 can be direct outputs of the asset-specific analysis or can be external portfolio variables that have been predefined or pre-computed prior to the network analysis.

In one embodiment, the output node 606 may also be connected to other nodes defined previously via either a directed or undirected edge. Each edge may have a corresponding conditional probability function that provides the complete probabilistic description of the output of the node it connects to. Deterministic dependencies may also be modelled by setting the conditional probabilities to binary values. Hence, three types of basic dependencies may be captured by this network structure, namely: fault-tree, Bayesian network, Markov network. These network models represent directed deterministic dependence, directed probabilistic dependence and undirected probabilistic dependence, respectively. This network structure allows the modelling of strong interdependent processes and the impacts of natural peril while preserving the causal relationships between process impacts and damage of the portfolio as well as the capability to explicitly propagate uncertainties in the portfolio risk analysis. This type of simulation can be done at a by-realization basis, and is therefore capable of generating probabilistically consistent descriptions of damage, loss and impacts to interdependent processes in a multi-peril context.

Figure 7:
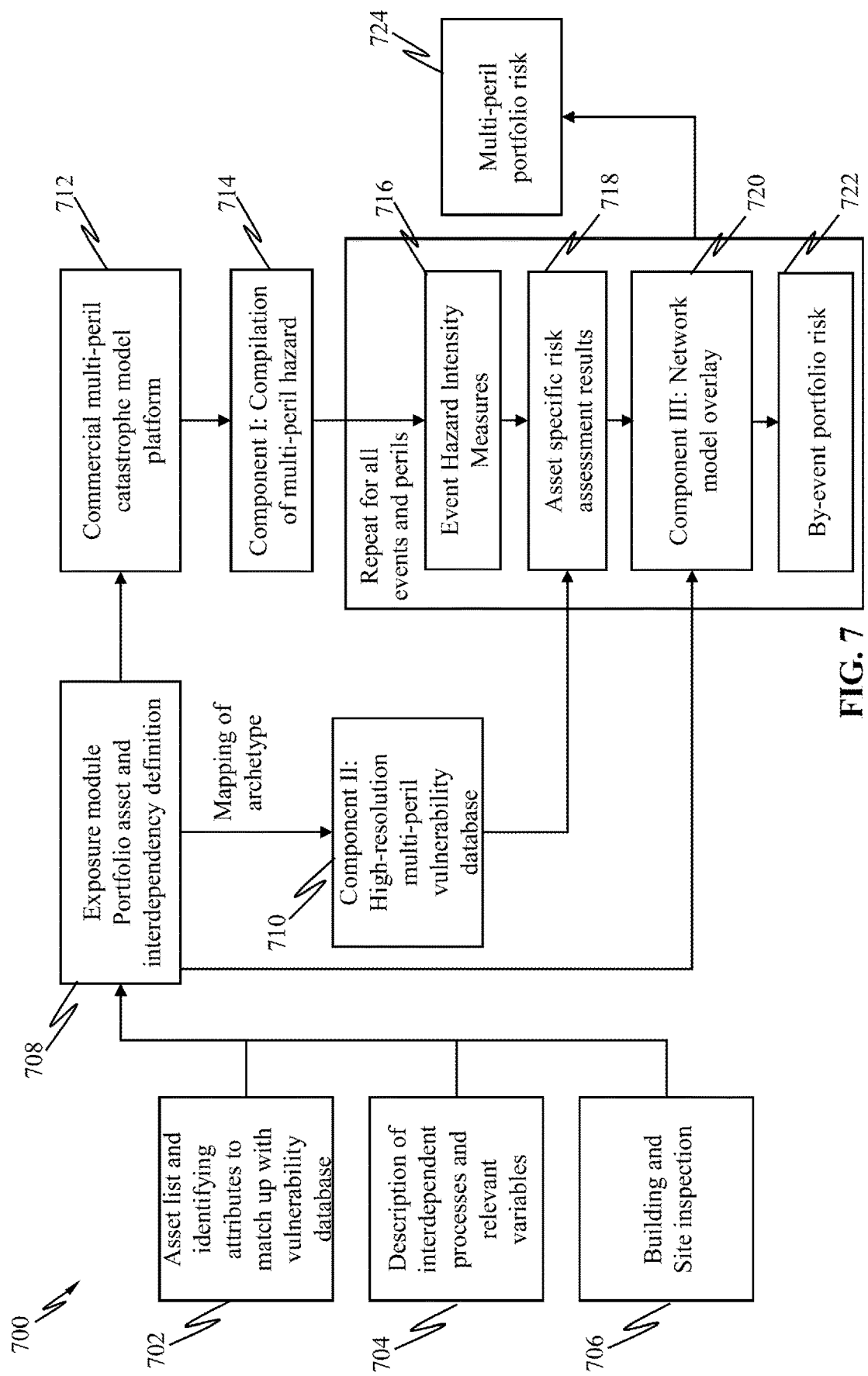
FIG. 7 illustrates a system 700 for building-specific multi-peril risk assessment and mitigation, in accordance with an embodiment.

FIG. 7 illustrates a system 700 for building-specific multi-peril risk assessment and mitigation, in accordance with an embodiment. The system may comprise an exposure module 708, a multi-peril catastrophe model platform 712, a multi-peril hazard module 204, a database 206 and a graphical network module 208.

The exposure module 708 may receive data pertaining to asset list and identifying attributes to match up with vulnerability database 702, data pertaining to description of interdependent processes and relevant variables 704, and building and site inspection data 706. The exposure module 708 may comprise data related to portfolio asset and process interdependency definition.

Typically, the exposure module 708 describes the portfolio of structures by their specific location, building attributes such as year built, type of construction, number of storeys, other optional modifiers such as whether the building meets code requirements associated with the peril of interest.

Further, the exposure module 708 may map each of the asset to a building archetype.

The multi-peril catastrophe model platform 712 may comprise hazard information for multiple perils.

The multi-peril hazard module 204 may obtain the hazard information to create a multi-peril event catalogue configured to generate event hazard intensity measures 716.

The database 206 may comprise high-resolution multi-peril vulnerabilities functions 710. The processor 202 may determine building-specific risk assessment results 718 based on the event hazard intensity measures 716 and vulnerabilities functions 710.

The graphical network module 208 may generate probabilistic networks 720 for wherein the probabilistic networks are connected to the determined building-specific risk assessment results 718 of the peril vulnerability functions that have strong interdependencies. Further, the system may determine the multi-peril risk 722 associated with the building.

In one embodiment, the processor 202 may be further configured to generate a mitigation solution for the determined multi-peril risk for the building.

The system may cost-efficiently and quickly generate high-resolution multi-peril risk assessment that are probabilistically consistent and are suitable for decision-support for owners of individual assets.

The system may enable integration of asset interdependency maps as part of portfolio impact assessment.

The system may enable multi-peril event-based risk analysis for portfolios of assets that have the capability to preserve inter-peril correlation and intra-event correlation.

The system may cause rapid generation of mitigation solutions for multiple perils and presents quantitative cost and benefit of all generated risk mitigation options.

The system may enable explicit evaluation and optimization of portfolio risk mitigation plans against multiple perils implemented over time (incremental risk mitigation).

The system may compactly represent the performance of large numbers of multi-peril natural hazard risk mitigation solutions in graphical form for decision makers.

The system may enable stakeholders to accurately assess the quantifiable property-specific financial, downtime, safety and other operational impacts due to multiple natural peril exposure for long-term maintenance and risk management plans.

The system may enable stakeholders of portfolio containing similar properties to perform rapid and high accuracy multi-peril risk assessment and mitigation analysis.

The system may enable stakeholders of general multi-property portfolios to quantitatively assess and optimize practical options of incremental multi-peril risk mitigation over a period of time.

The system may enable stakeholders to identify the breakdown of components that contribute to the overall risk to identify cost-effective solutions that may be different from other existing guidelines/engineering standards based only on achieving code-based life-safety performance.

The system may enable portfolio owners to identify the breakdown of building properties that contribute to the overall portfolio seismic risk.

The system may enable portfolio owners and managers to properly prioritize and allocate limited temporal, financial and human resources to manage seismic risk based on a multifaceted natural hazard impact analysis.

The system may enable stakeholders to identify critical elements in interdependent network of assets and the quantitative contribution to risk for targeting mitigation.

The system may enable the construction of rational, and quantitative arguments for justifying various degrees of natural hazard risk mitigation and resilience interventions.

The system may promote the wide-spread use of cost-effective resilience planning by enabling the building of business cases based on rational and quantitative cost-benefit analysis.

The system may enable owners and developers to realize upfront cost-savings relative to existing prescriptive code-based approach that relies heavily on conventional engineering code approaches.

The system may enable owners and stakeholders to obtain better and more rationally developed insurance policies for multiple-perils.

The system may enable owners and stakeholders to actively natural disaster direct and indirect losses.

The system may promote a safer and more resilient building environment and society that resists damage and quickly recovers from catastrophic natural hazard events.

The processes described above is described as a sequence of steps, this was done solely for the sake of illustration. Accordingly, it is contemplated that some steps may be added, some steps may be omitted, the order of the steps may be re-arranged, or some steps may be performed simultaneously.

The example embodiments described herein may be implemented in an operating environment comprising software installed on a computer, in hardware, or in a combination of software and hardware.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications, these should not be construed as limiting the scope of the invention but as merely providing illustrations of some of the personally preferred embodiments of this invention.

What is claimed is:

1. A system for building-specific multi-peril risk assessment and mitigation, the system comprises:
   a multi-peril hazard module configured to:
      obtain hazard information related to at least a building for multiple perils; and
      create a multi-peril event catalogue for the multiple perils, wherein the multi-peril event catalogue is configured to generate intensity measures for each of the multiple perils;
   a processor configured to:
      derive a peril vulnerability function for each of the multiple perils for an archetype of the building, wherein the peril vulnerability function relates to a consequence of interest corresponding to the archetype of the building; and
      determine building-specific risk assessment results based on the hazard information and the peril vulnerability function;
   a database configured to:
      store the derived plurality of peril vulnerability functions for the multiple perils corresponding to each of the archetypes of buildings; and
   a graphical network module configured to:
      create probabilistic networks, wherein the probabilistic networks are connected to the determined building-specific risk assessment results of the peril vulnerability functions that have strong interdependencies; and
      determine a multi-peril risk associated with the building.

2. The system of claim 1, wherein the multi-peril hazard module is configured to obtain hazard information from a multi-peril catastrophe model platform.

3. The system of claim 1, wherein the processor is further configured to generate a mitigation solution for the determined multi-peril risk for the building.

4. The system of claim 1, wherein to derive the peril vulnerability function for a building archetype and a peril of interest, the processor is configured to:
   receive the intensity measures corresponding to the peril of interest;
   determine engineering demand parameters of the building archetype based on the received intensity measures;
   perform damage analysis using the determined engineering demand parameters on each component of the building archetype;
   determine the consequences of interest based on the damage analysis; and
   derive the peril vulnerability function for each of the consequence of interest corresponding to the peril of interest, wherein the peril vulnerability function relates the intensity measures with the consequence of interest.

5. The system of claim 4, wherein the processor is configured to determine engineering demand parameters based on dynamic analysis of the building archetype.

6. The system of claim 4, wherein to perform damage analysis, the processor is configured to:
   process the engineering demand parameters to derive a smooth joint distribution; and
   generate individual realizations of engineering parameters directly correlated to the component damage in the building.

7. The system of claim 6, wherein the output node of the probabilistic network is connected to an independent variable via a directed edge.

8. The system of claim 6, wherein the output node of the probabilistic network is connected to other nodes via a directed edge or undirected edge.

9. The system of claim 4, wherein the processor is configured to perform damage analysis using Monte Carlo sampling.

10. The system of claim 1, wherein the multi-peril event catalogue is configured to generate the intensity measures for multiple perils on by-event basis.

11. The system of claim 1, wherein the event catalogue is configured to generate the intensity measures for multiple perils on by-peril basis.

12. The system of claim 11, wherein the multi-peril hazard module is configured to convert the event based risk information into hazard information using a monotonic invertible vulnerability function.

13. The system of claim 1, wherein the multi-peril hazard module is configured to receive location information of the building and obtain the hazard information based on the location information of the building.

14. The system of claim 1, wherein when the spatial correlation between buildings is not required, the multi-peril event catalogue is configured to generate intensity measures based on hazard maps.

15. The system of claim 1, wherein when the spatial correlation between buildings is required, the multi-peril event catalogue is configured to generate intensity measures using a stochastic event catalogue or event based risk information.

16. The system of claim 1, wherein the multi-peril hazard module is configured to obtain hazard information by web crawling.

17. The system of claim 1, wherein each of the probabilistic networks is connected to single type of building-specific risk assessment result via an output node.

18. A method for building-specific multi-peril risk assessment and mitigation, the method comprises the steps of:
  obtaining hazard information related to at least a building for multiple perils;
  creating a multi-peril event catalogue for the multiple perils, wherein the multi-peril event catalogue is configured to generate intensity measures for each of the multiple perils;
  deriving a peril vulnerability function for each of the multiple perils for an archetype of the building, wherein the peril vulnerability function relates to a consequence of interest corresponding to the archetype of the building;
  determining building-specific risk assessment results based on the hazard information and the peril vulnerability function;
  creating probabilistic networks, wherein the probabilistic networks are connected to the determined building-specific risk assessment results of the peril vulnerability functions that have strong interdependencies; and
  determining a multi-peril risk associated with the building.

19. The method of claim 18, wherein the method comprises generating a mitigation solution for the determined multi-peril risk for the building.

20. The method of claim 18, wherein deriving the peril vulnerability function for a peril comprises:
  receiving the intensity measures corresponding to the peril for which the peril vulnerability function is to be derived;
  analyzing the multiple intensity measures for determining engineering demand parameters of the building;
  performing damage analysis using the determined engineering demand parameters on each component of the building;
  determining the consequence of interest based on the damage analysis; and
  deriving a peril vulnerability function for the consequence of interest, wherein the peril vulnerability function relates the intensity measures with the consequence of interest.

21. The method of claim 20, wherein performing damage analysis comprises:
  processing the engineering demand parameters to derive a smooth joint distribution; and
  generating individual realizations of engineering parameters directly correlated to the component damage in the building.

* * * * *